(12) United States Patent
Huhta

(10) Patent No.: US 6,628,394 B2
(45) Date of Patent: Sep. 30, 2003

(54) OPTICAL GASKET SYSTEM

(75) Inventor: Jeffrey M. Huhta, Loveland, CO (US)

(73) Assignee: Hach Company, Loveland, CO (US)

( * ) Notice: Subject to any disclaimer, the term of this patent is extended or adjusted under 35 U.S.C. 154(b) by 107 days.

(21) Appl. No.: 09/777,195

(22) Filed: Feb. 2, 2001

(65) Prior Publication Data

US 2001/0033379 A1 Oct. 25, 2001

Related U.S. Application Data

(60) Provisional application No. 60/184,984, filed on Feb. 25, 2000.

(51) Int. Cl.[7] ............................................... G01N 21/04
(52) U.S. Cl. ...................................... 356/402; 356/410
(58) Field of Search ............................... 356/402, 410, 356/411, 440

(56) References Cited

U.S. PATENT DOCUMENTS

| | | | | |
|---|---|---|---|---|
| 3,062,963 A | * | 11/1962 | Douty ........................ 356/402 |
| 3,435,209 A | * | 3/1969 | Keahl ........................ 356/402 |
| 4,193,694 A | * | 3/1980 | Smith ........................ 356/407 |
| 4,324,758 A | * | 4/1982 | Eisentraut et al. ............ 422/61 |
| 5,078,493 A | * | 1/1992 | Evens et al. ................. 356/246 |
| 5,872,361 A | * | 2/1999 | Paoli et al. ............... 250/341.8 |
| 5,969,812 A | * | 10/1999 | Carver ........................ 356/319 |
| 5,991,048 A | * | 11/1999 | Karlson et al. .............. 356/445 |

* cited by examiner

Primary Examiner—Daniel St. Cyr
(74) Attorney, Agent, or Firm—Dean P. Edmundson

(57) ABSTRACT

An optical gasket system for use in a colorimeter or other instrument which utilizes a light beam and a sample cell or chamber for a liquid to be tested. Each gasket is optically clear and is pliable so as to conform to the surface of the sample cell which is in the path of the light beam. The gaskets prevent moisture from condensing on the surface of the sample cell and interfering with the passage of the light beam through the cell.

8 Claims, 4 Drawing Sheets

OPTICAL GASKET SYSTEM

CROSS-REFERENCE TO RELATED APPLICATION

This application is based upon, and claims the benefit of, my Provisional Application No. 60/184,984, filed Feb. 25, 2000.

FIELD OF THE INVENTION

This invention relates to colorimeters and other instruments which use a light beam and a photodetector. More particularly, this invention relates to the use of optical gaskets or seals in colorimeters or other instruments.

BACKGROUND OF THE INVENTION

Colorimeters utilize a light beam, a sample cell or chamber (usually glass), and a photodetector. The light beam is normally passed through a liquid sample (contained in the cell or chamber) and one or more color filters before reaching the detector. A glass window may also be positioned in the light beam on each side of the sample cell.

When the liquid sample in the sample cell is cool and there is sufficient humidity in the ambient air, moisture will condense on the surface of the sample cell. Such condensation in the path of the light beam will interfere with the passage of light through the cell and thereby interfere with the accuracy of the testing.

There has not heretofore been provided an optical gasket system having the features and advantages provided by the system of the present invention.

SUMMARY OF THE INVENTION

In accordance with the present invention there is provided an optical gasket system for a colorimeter or other instrument which utilizes a light beam and a sample cell or chamber for a liquid to be tested. In a preferred embodiment, the system of the invention comprises the placement of an optically clear and pliable gasket or seal in contact with the surface(s) of the sample cell or chamber which is in the path of the light beam. The presence of the gasket or seal in intimate contact with the surface of the sample cell or chamber prevents moisture from condensing on such surface and thereby avoids the problem of condensation interfering with the passage of the light beam through the cell.

Although the gasket system of the invention is especially useful in conjunction with a colorimeter, it also has utility in other types of instruments which utilize a light beam and a sample cell or chamber (e.g. turbidimeter, reflectometer, particle counter, etc.).

Other features and advantages of the optical gasket system of this invention will be apparent from the following detailed description and the accompanying drawings.

BRIEF DESCRIPTION OF THE DRAWINGS

The invention is described in more detail hereafter with reference to the accompanying drawings, wherein like reference characters refer to the same parts throughout the several views and in which.

DETAILED DESCRIPTION OF THE INVENTION

Figure 1:
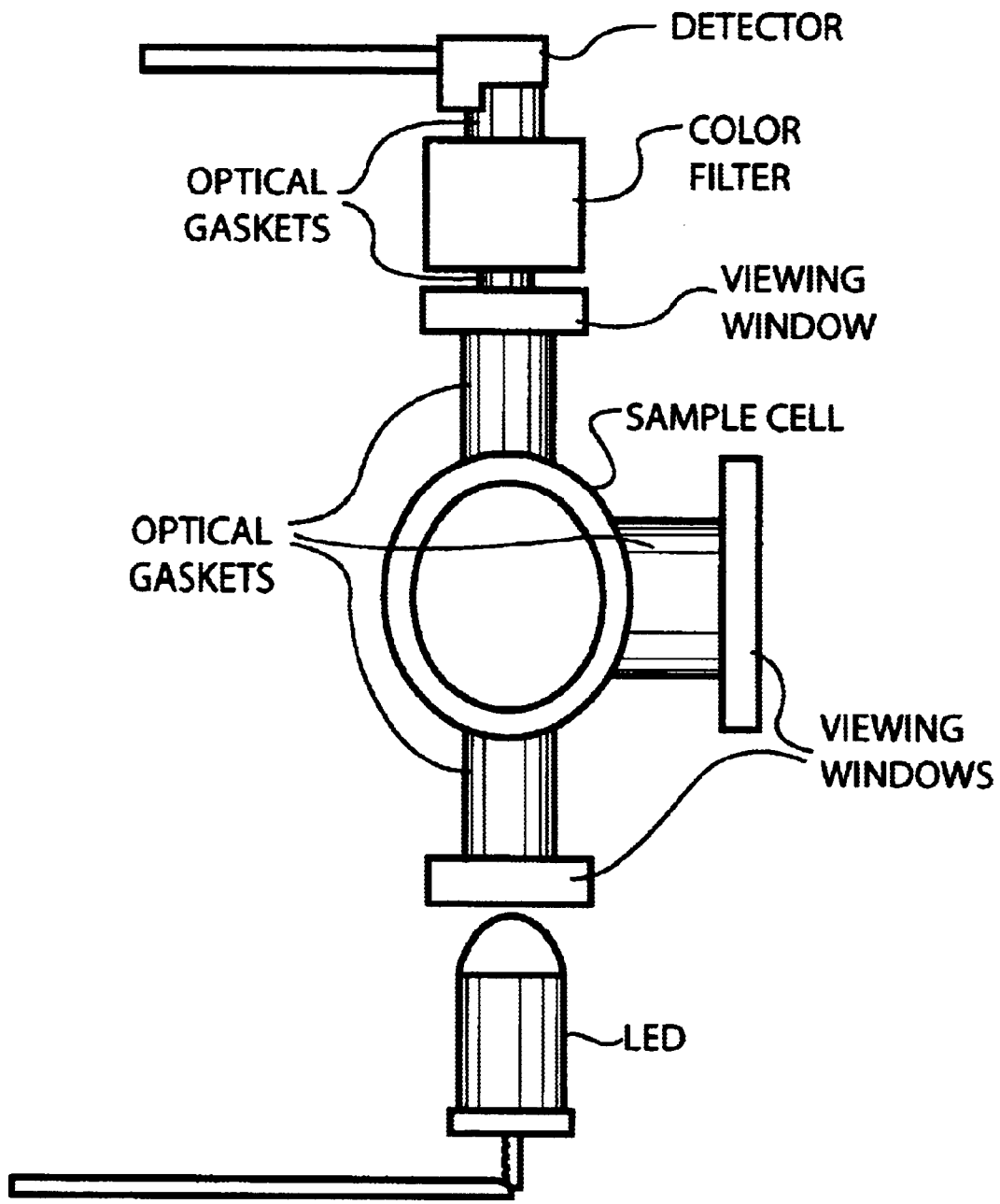
FIG. 1 is a schematic diagram of a colorimeter in which the gasket system is being used.
Figure 2:
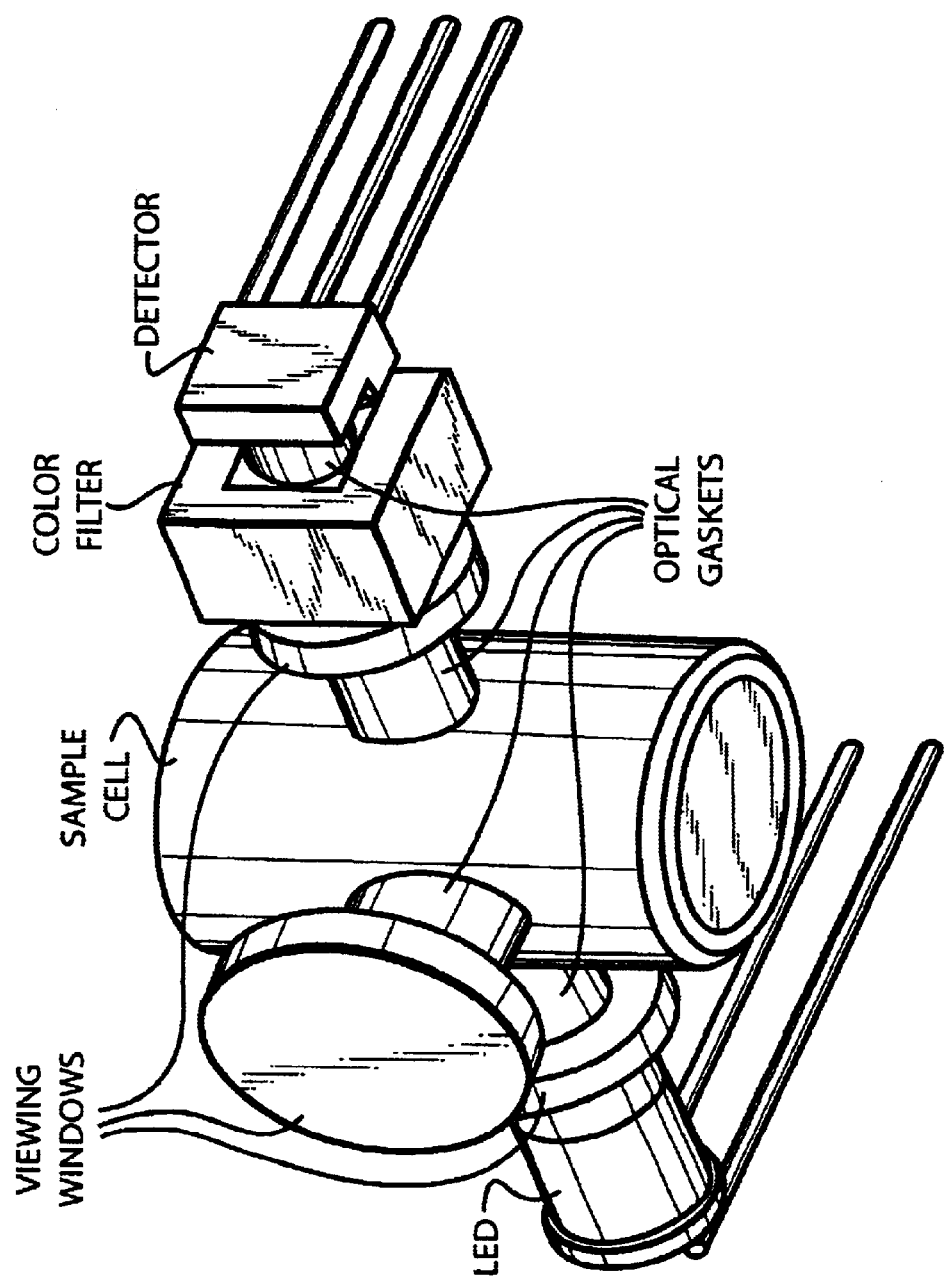
FIG. 2 is an isometric view showing one manner in which the optical gaskets may be used in a colorimeter.

In the drawings there is shown a colorimeter which includes an LED (light emitting diode) light source, a glass sample cell, color filter and a photodetector (e.g. a light-to-frequency detector). Three glass windows are also shown. One glass window is located adjacent to the LED in the path of the light beam, one is adjacent to the color filter in the path of the light beam, and the other is located to one side of the sample cell (as a viewing port for a user to observe color development in the sample cell) and out of the path of the light beam. The colorimeter includes a sample inlet, reagent inlet, and a drain. The instrument is capable of performing on-line analysis of a liquid sample (e.g. water).

Figure 3:
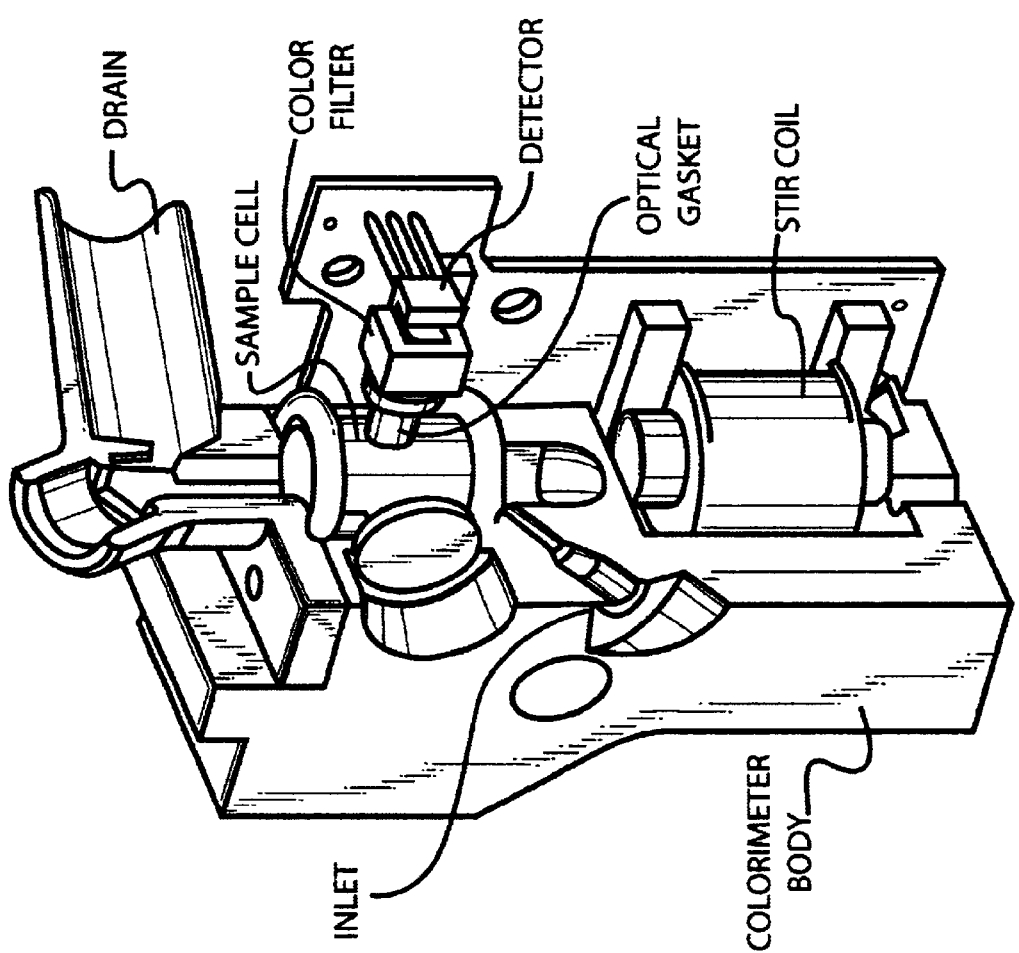
FIG. 3 is a cut-away view showing the position of the components of FIG. 2 in a colorimeter block.
Figure 4:
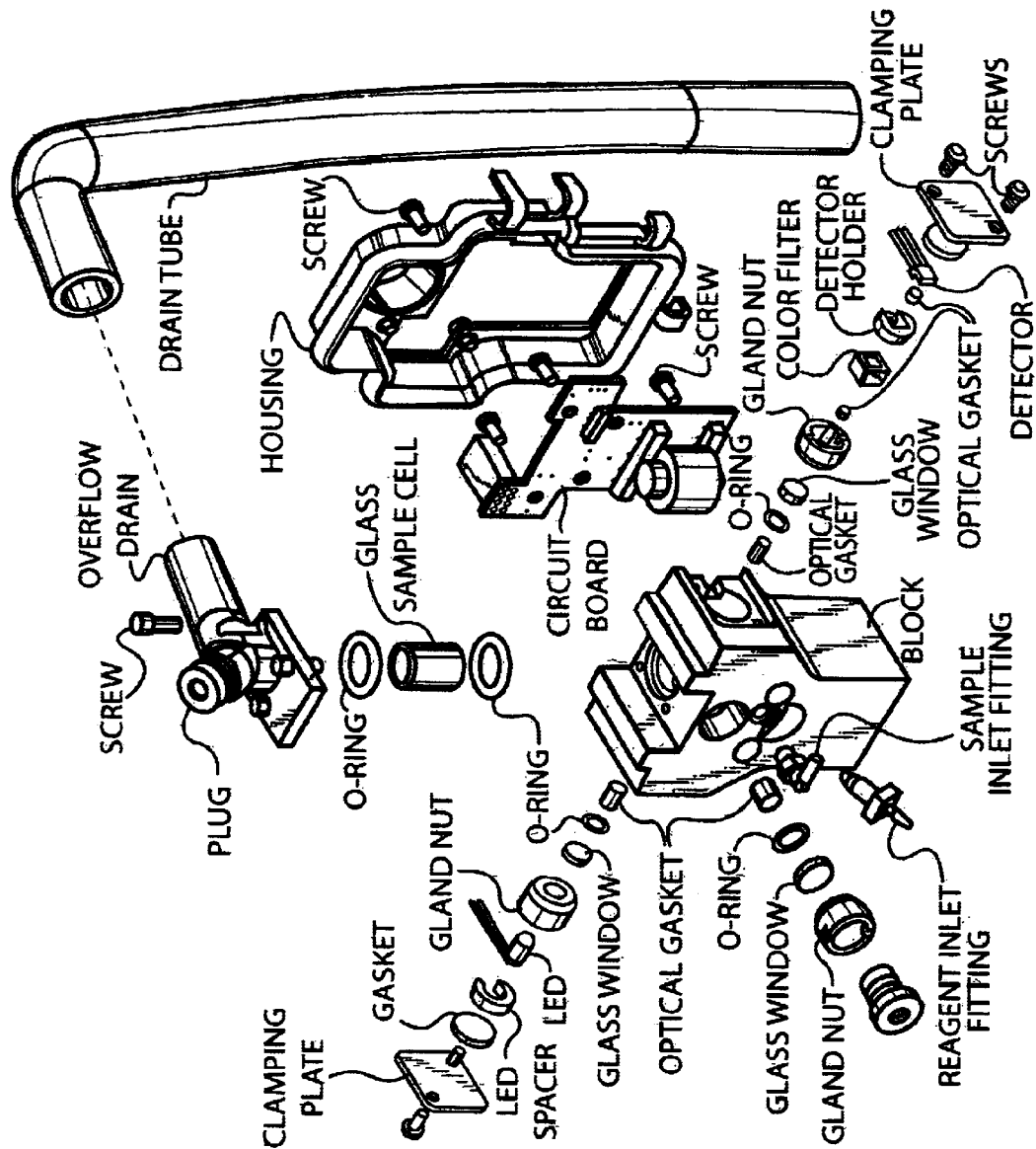
FIG. 4 is an exploded view of a colorimeter in which optical gaskets are being used.

An optical gasket is positioned on each side of the sample cell, in the path of the beam, and is in intimate contact with the outer surface of the sample cell and one of the glass windows shown. Gland nuts and clamping plates are used to secure this entire assembly in the colorimeter block which is shown in FIG. 3. When the gland nuts are tightened, the optical gaskets are caused to become compressed between the surface of the sample cell and the surface of a respective glass window. This assures that there is intimate contact between each optical gasket, the surface of the cell, and a respective glass window.

The optical gaskets are preferably cast in cylindrical shapes and inserted into the appropriate spots or locations in the colorimeter block during assembly. No adhesive is required to keep the gaskets in place. All fastening is done using a system of conventional threaded gland nuts to assure that appropriate compression is maintained on the optical gaskets. Many other geometrical shapes for the optical gasket may be used.

The gaskets conform to the round surface of the sample cell, as well as the flat surface of the windows, and any small imperfections become transparent when the gasket material is compressed against the surfaces of the window and the cell. When the assembly is complete with each of the optical gaskets in place, there is essentially no air space within the optical path or the viewing path on the view port.

The optical gaskets may be manufactured using standard casting procedures and an optically clear grade of silicone (preferably). One such material, manufactured by Wacker, is identified as ELASTOCIL® M4647 RTV-2 silicon rubber. It is a pourable, addition-curing, two-component, high strength silicone compound that vulcanizes at room temperature. This material is typically used for making silicone molds, particularly for reproducing parts using polyurethane or epoxy resins. This silicone is optically transparent and does not reduce the light throughput by any measurable amount. A colorimeter takes a reference reading during each cycle, and accordingly any optical anomalies due to the optical gasket get zeroed out. Preferably, the cured gasket material is not colored. It is also necessary for the gasket material to be pliable and compressible so that it can conform to the curved surfaces of the sample cell. The material should exhibit a compression characteristic in the range of about 5 to 20% (preferably 10 to 15%).

The size and shape of the optical gasket may vary. Preferably the gasket will fill a sufficient volume in the instrument such that there is no air space within the optical path or the viewing path.

Other types of known materials can be used for the optical gaskets (e.g. urethanes) so long as the gasket exhibits the physical properties described herein.

Other variants are possible without departing from the scope of this invention.

What is claimed is:

1. An optical gasket system for use in a light path of an instrument including a light source, sample cell, and a photodetector, wherein said system comprises an optical gasket positioned in said light path to exclusion of air in said light path, wherein said optical gasket is optically clear and exhibits a compression characteristic in a range of about 5 to 20%.

2. The system in accordance with claim 1, wherein said gasket comprises silicone.

3. The system in accordance with claim 1, wherein said gasket exhibits a compression characteristic in a range of about 10 to 15%.

4. The system in accordance with claim 1, wherein said gasket has a cylindrical shape.

5. A colorimeter having a light source for emitting a light beam, a sample cell and a photodetector, comprising a first optical gasket positioned in a path of said light beam between said light source and said sample cell and a second optical gasket positioned between said sample cell and said photodetector to exclusion of air in said path of said light beam, wherein each said optical gasket is optically clear.

6. The colorimeter in accordance with claim 5, wherein said optical gasket comprises silicone.

7. The colorimeter in accordance with claim 5, wherein each said optical gasket exhibits a compression characteristic in a range of about 5 to 20%.

8. The colorimeter in accordance with claim 5, further comprising a first glass window between said light source and said sample cell and a second glass window between said photodetector and said sample cell; wherein said first optical gasket is in intimate contact with said first glass window and said sample cell, and said second optical gasket is in intimate contact with said second glass window and said sample cell.

* * * * *